United States Patent [19]

Galbraith

[11] Patent Number: 4,592,359
[45] Date of Patent: Jun. 3, 1986

[54] MULTI-CHANNEL IMPLANTABLE NEURAL STIMULATOR

[75] Inventor: Douglas C. Galbraith, Stanford, Calif.

[73] Assignee: The Board of Trustees of the Leland Stanford Junior University, Stanford, Calif.

[21] Appl. No.: 719,231

[22] Filed: Apr. 2, 1985

[51] Int. Cl.$^4$ ............................................... A61N 1/36
[52] U.S. Cl. .................................................. 128/419 R
[58] Field of Search ........... 128/419 R, 419 E, 419 C, 128/419 G, 421–422

[56] References Cited

U.S. PATENT DOCUMENTS

| | | | |
|---|---|---|---|
| 3,179,890 | 4/1965 | Warner | 128/419 R |
| 3,646,940 | 3/1972 | Timm et al. | 128/419 E |
| 4,095,602 | 6/1978 | Leveen | 128/419 R |
| 4,390,023 | 6/1983 | Rise | 128/421 |
| 4,390,756 | 6/1983 | Hoffman et al. | 128/421 |
| 4,428,377 | 1/1984 | Zollner et al. | 128/419 R |
| 4,441,210 | 4/1984 | Hochmair et al. | 128/419 R |

Primary Examiner—William E. Kamm
Assistant Examiner—Mitchell J. Shein
Attorney, Agent, or Firm—Flehr, Hohbach, Test, Albritton & Herbert

[57] ABSTRACT

A combination of a transmitter and implantable receiver are disclosed wherein data is conveyed from transmitter to receiver utilizing a data format in which each channel to be stimulated is adapted to convey information in monopolar, bipolar or analog form.

The data format includes two types of code words: transition words in which one bit is assigned to each channel and can be used to create monopolar pulsatile or bipolar pulsatile waveforms; and amplitude words which can create analog waveforms one channel at a time.

An essential element of the output system is a current source digital to analog converter which responds to the code words to form the appropriate output on each channel. Each output is composed of a set of eight current sources, four with one polarity of current and the other four with the opposite polarity of current. In each group of four, the current sources are binarily related, I, 2I, 4I and 8I. In this arrangement each channel can supply 16 amplitudes times two polarities of current; meaning 32 current levels. This channel is simply a 5-bit digit to analog converter.

The output circuitry contains charge balance switches. These switches are designed to recover residual charge when the current sources are off. They are also designed to current limit during charge recovery if the excess charge is too great so that they do not cause neural damage.

Each channel charge balances (will not pass DC current or charge) and charge limits to prevent electrode damage and bone growth. The charge balancing is performed by the charge balancing switches and by the blocking capacitor. The charge limiting is performed by the blocking capacitor only.

The charge level on each channel is defined using a switch network ladder which combines a plurality of parallel connected switches; closure of each switch doubles the current level handed off from the previous switch.

9 Claims, 11 Drawing Figures

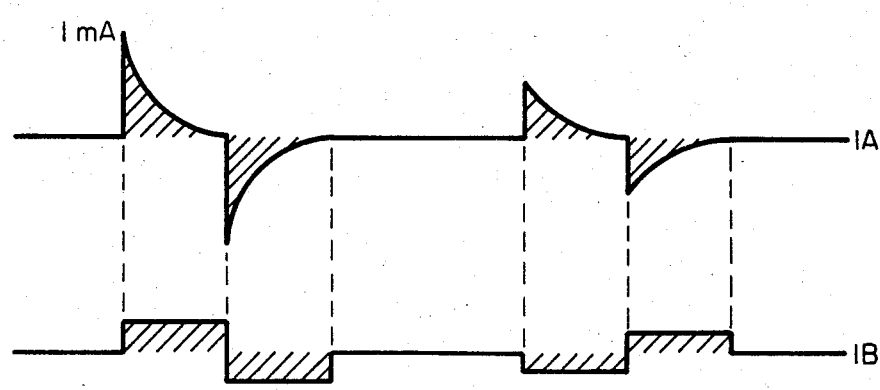
FIG_1
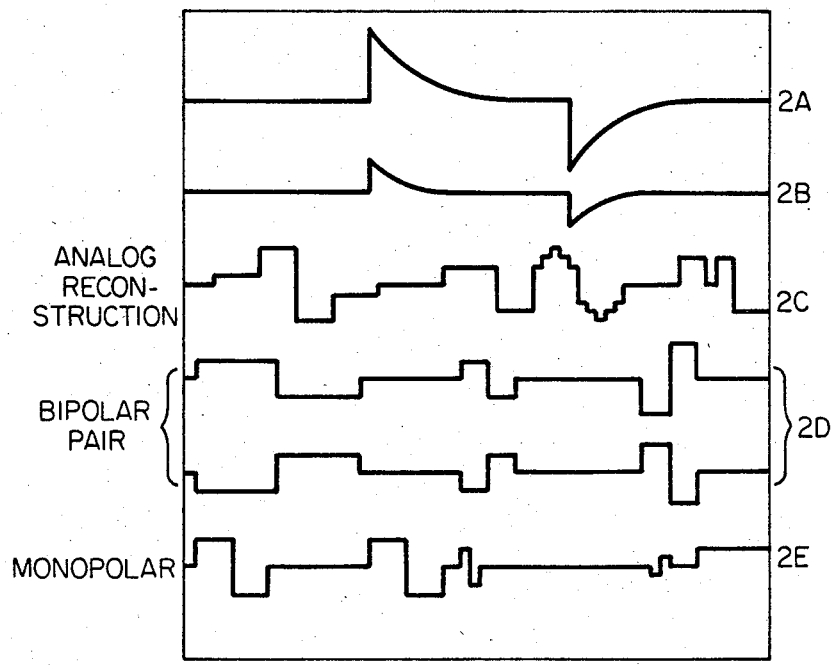
FIG_2

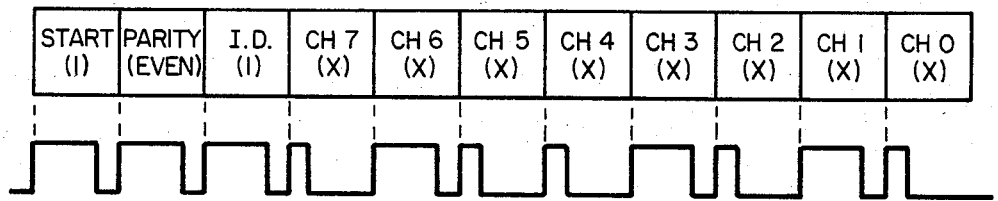
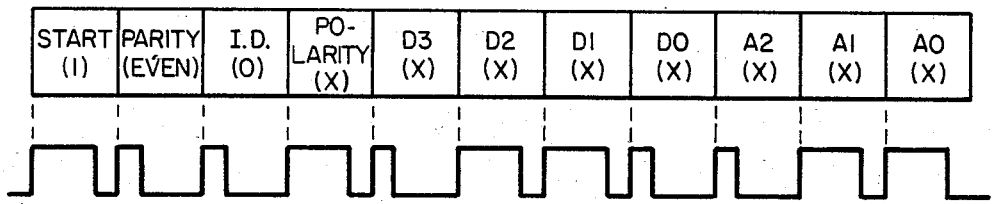
FIG_3
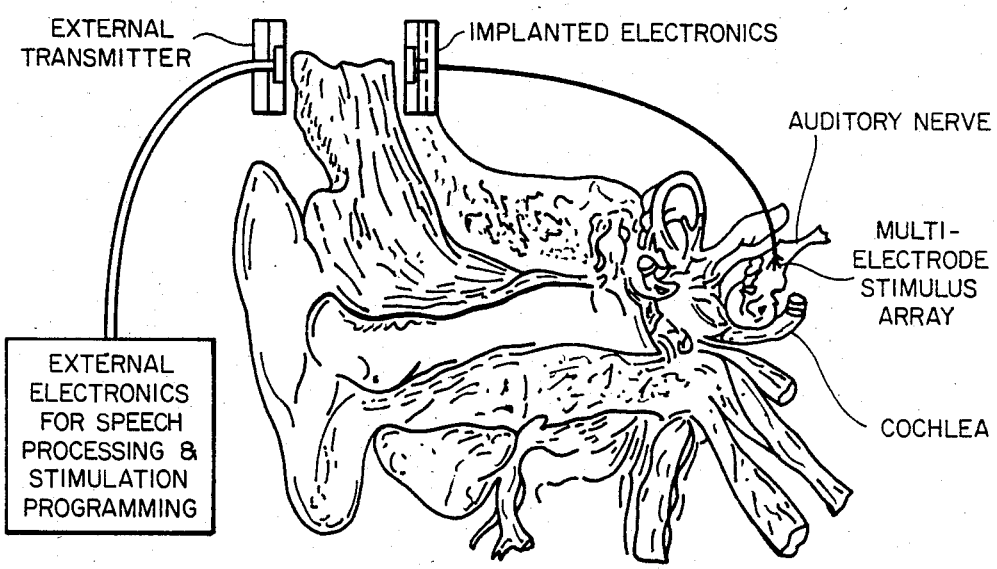
FIG_4

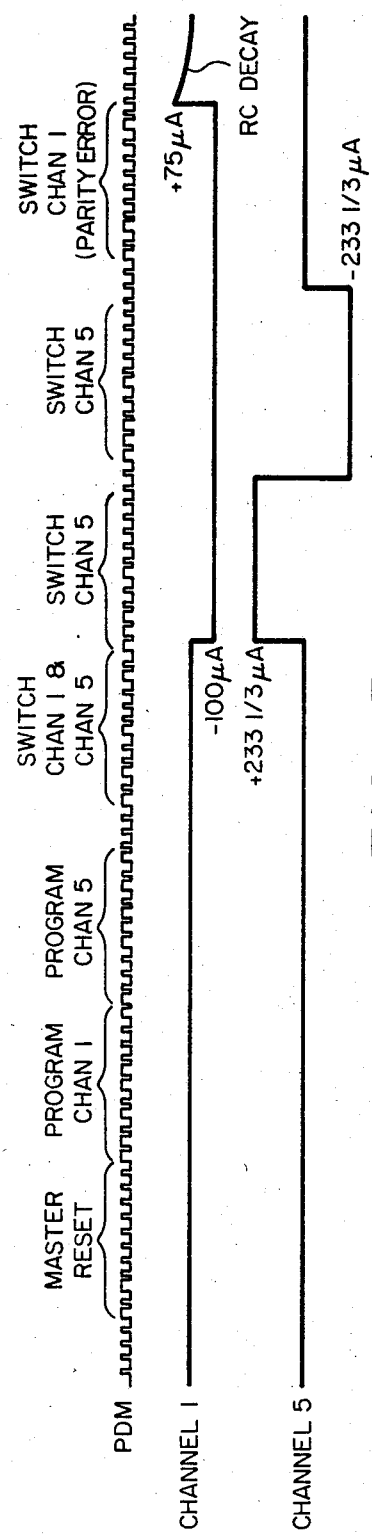
FIG_5
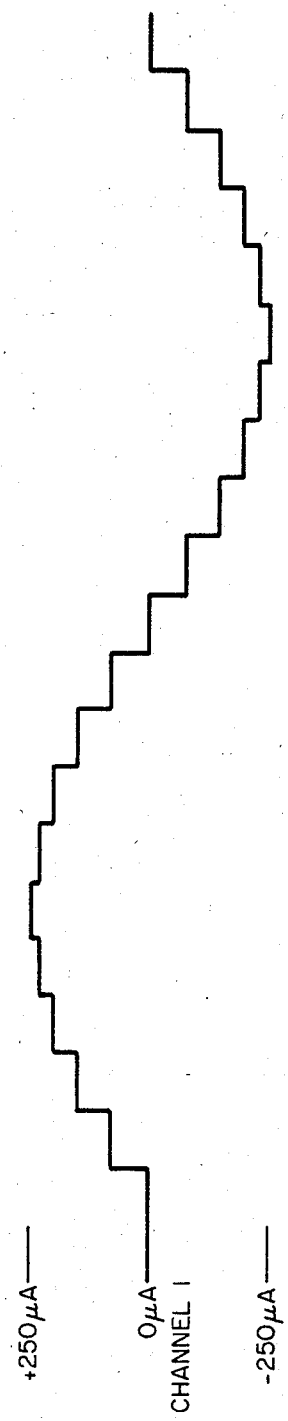
FIG_6

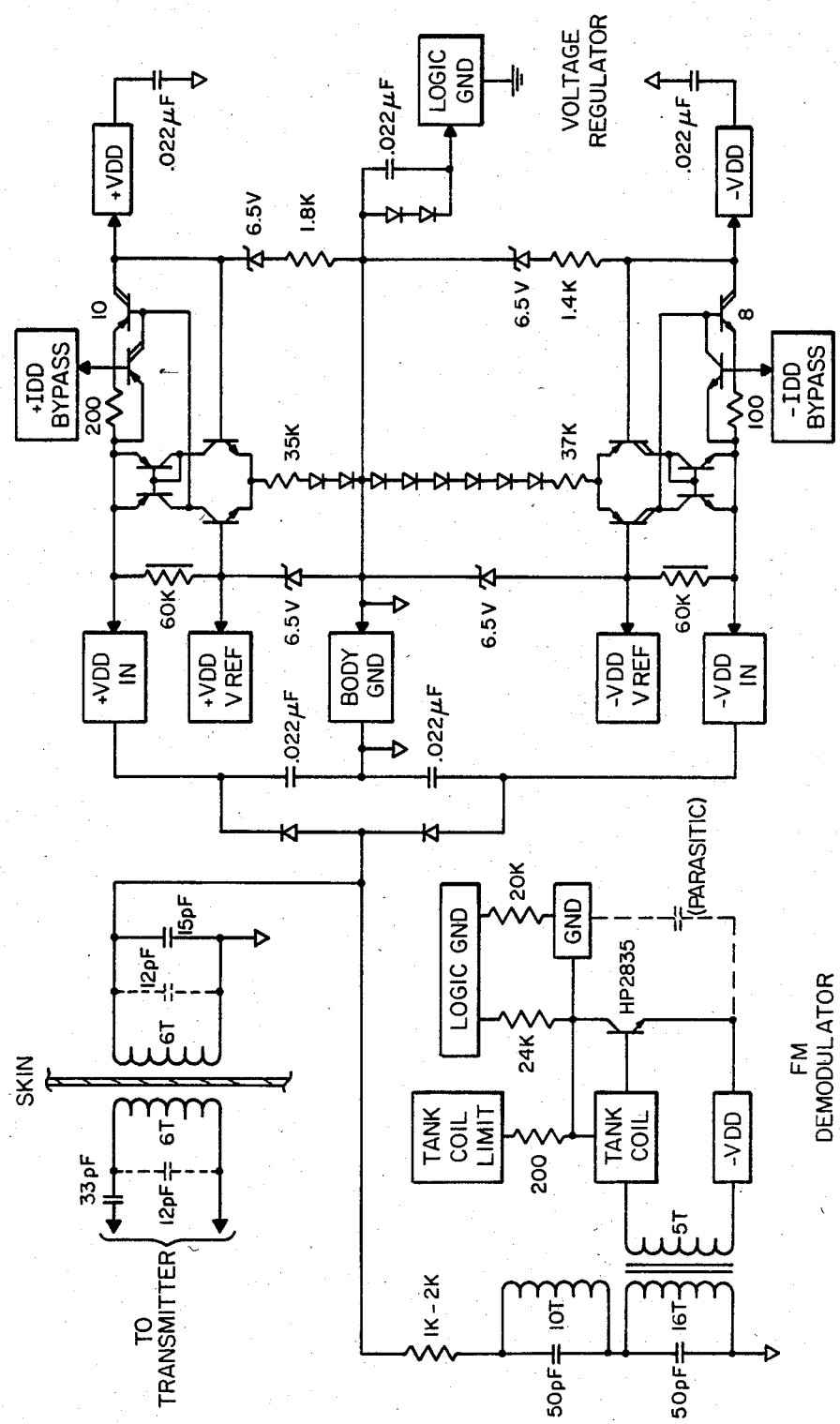
FIG_7

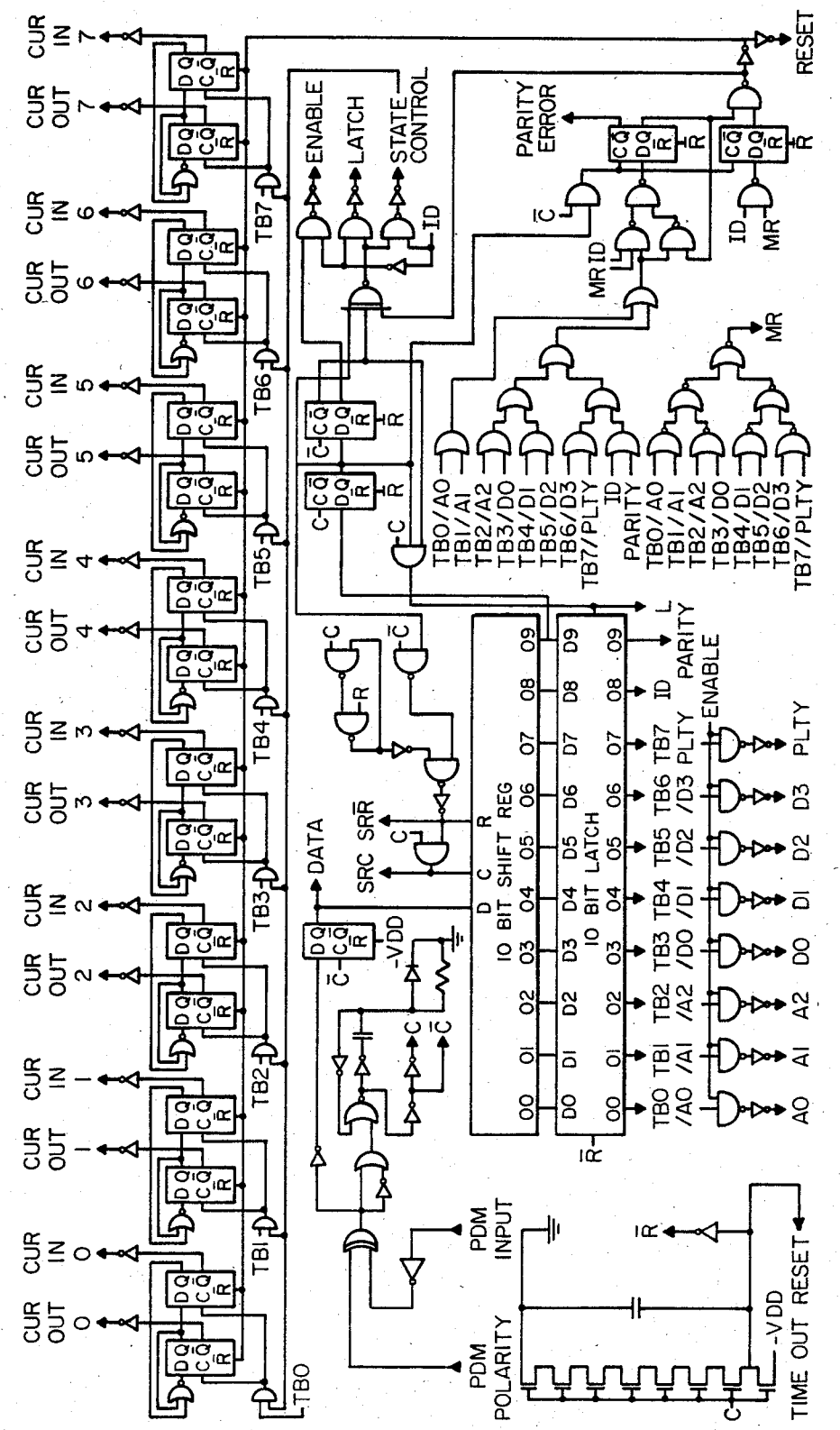
FIG_8A

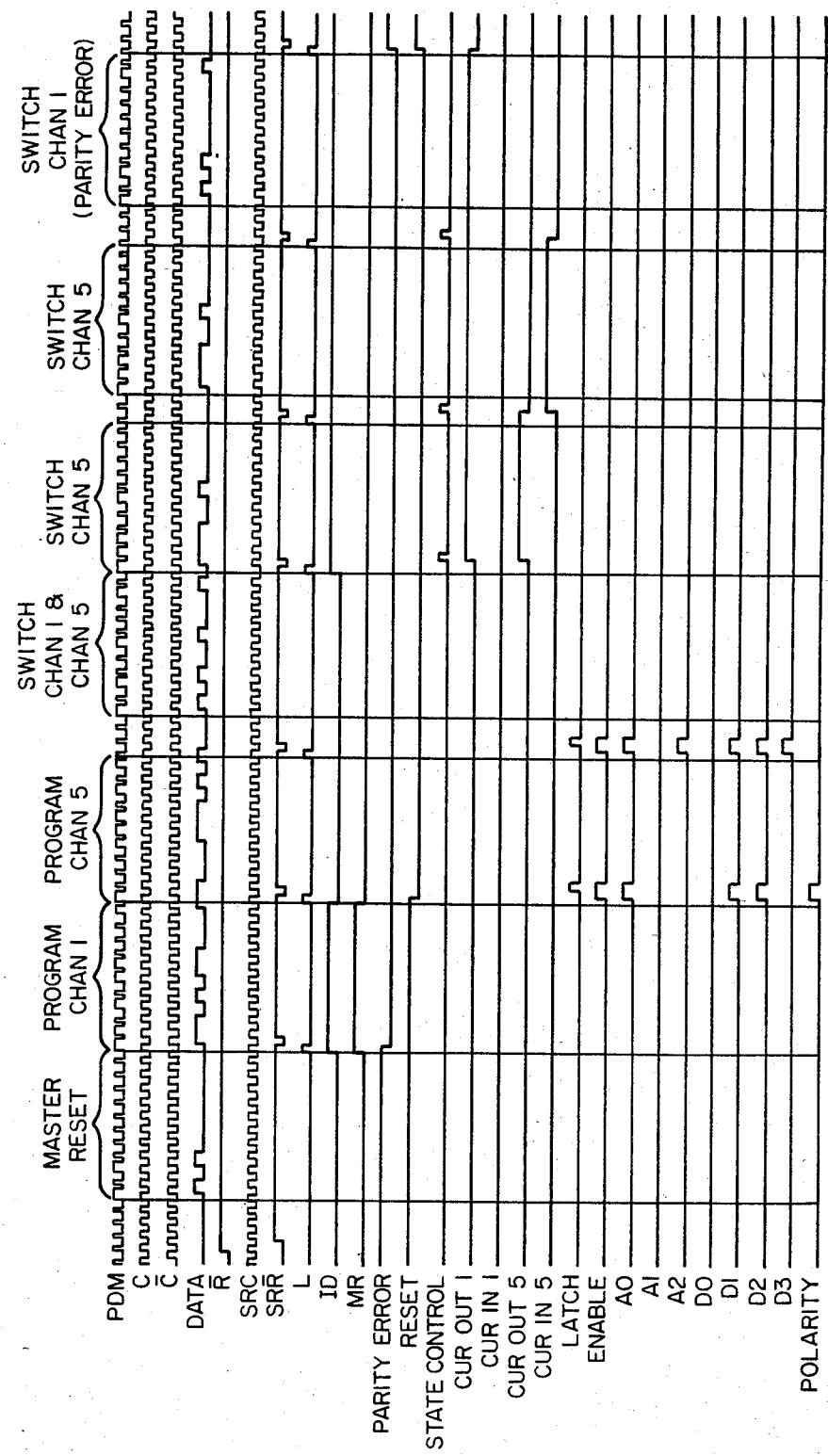
FIG_8B

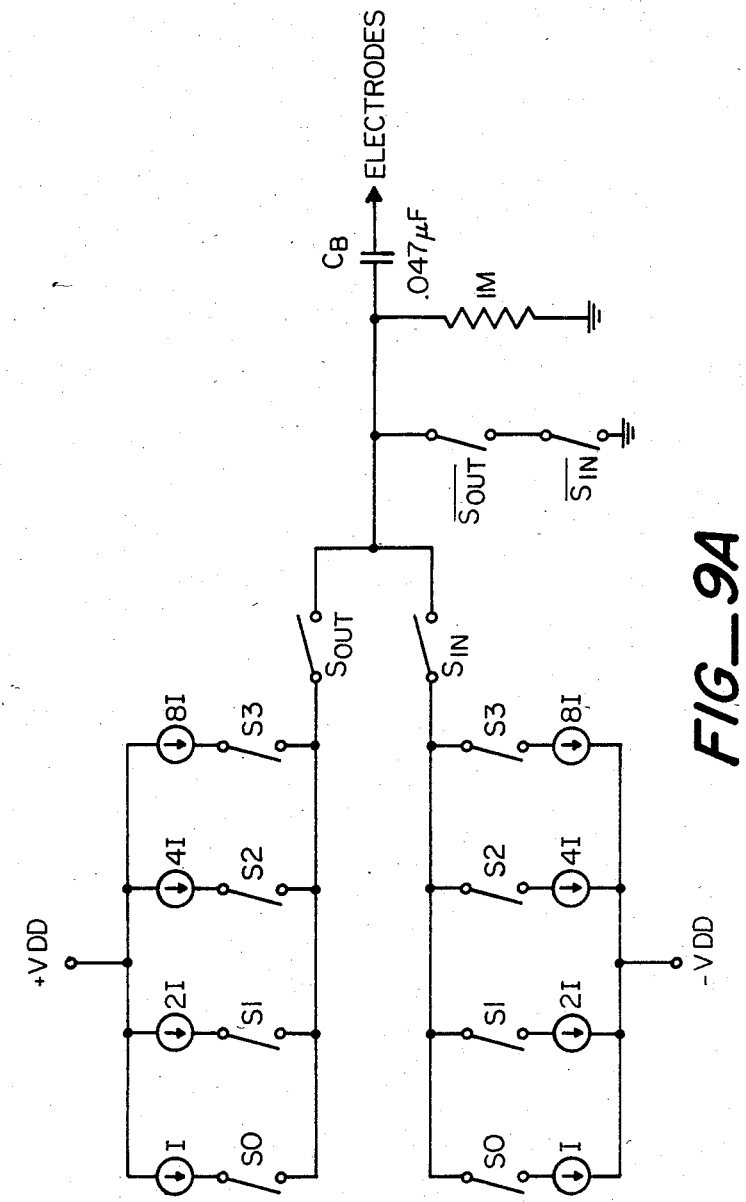
FIG_9A

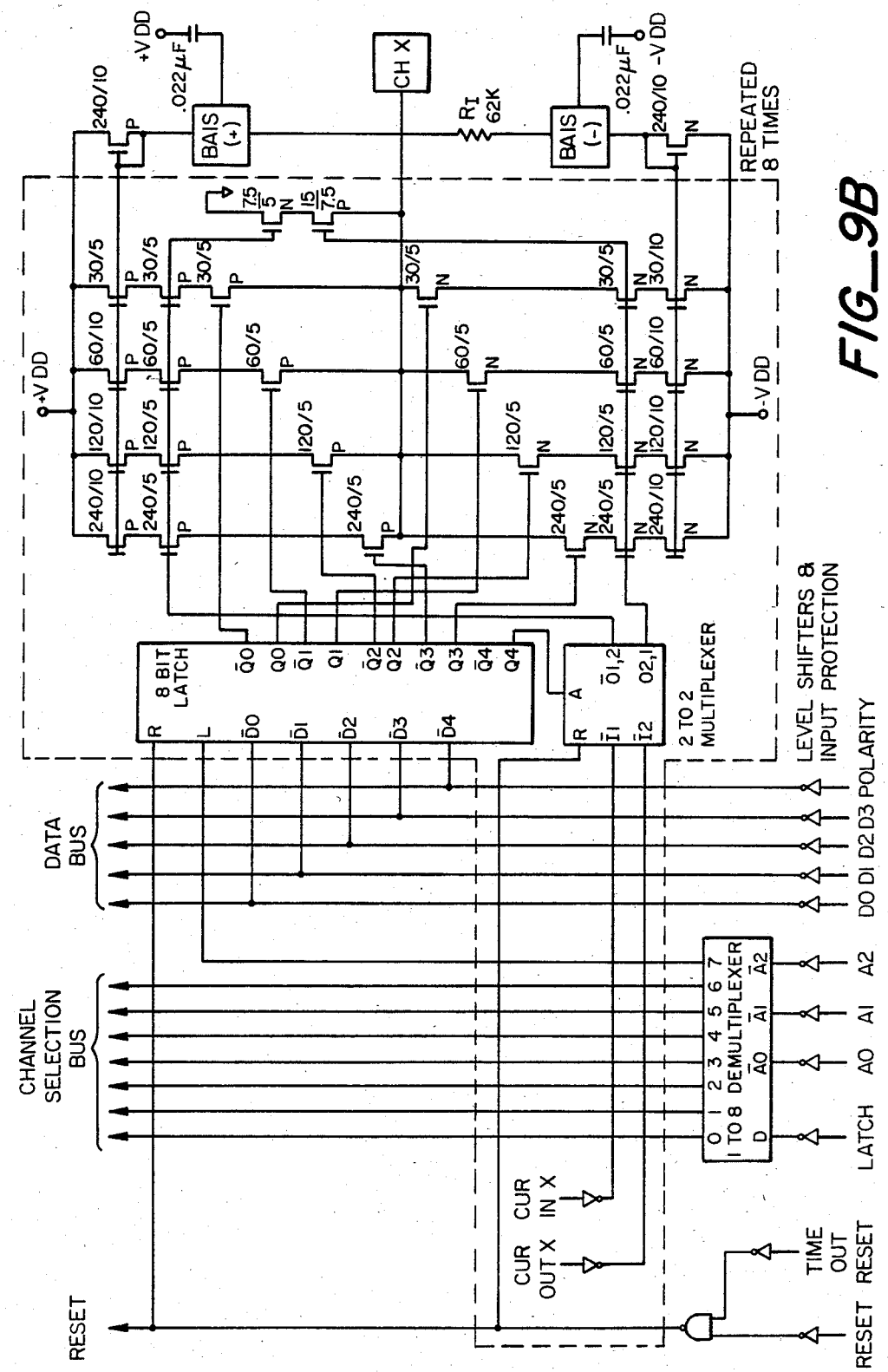
FIG._9B

MULTI-CHANNEL IMPLANTABLE NEURAL STIMULATOR

This invention is directed generally to the field of biomedical engineering and more particularly, the design of an implantable receiver stimulator of an auditory prosthesis system.

The profoundly deaf are individuals whose hearing loss is greater than 90 db. For most, no surgery or other treatment exists that can restore their hearing. The auditory prosthesis electrically stimulates neural tissue, producing the sensation of sound, restoring hearing to the profoundly deaf.

An auditory prosthesis system consists essentially of four parts: the speech processing hardware, the power and data transmitter, the implanted receiver/stimulator, and the implanted electrodes. The external electronics to perform the speech processing are the subject of a separated body of technology and are not a part of this patent application. The coupling through the skin is achieved using the simultaneously filed application of Mr. Galbraith entitled "A Wide Band Inductive Transdermal Power and Data Link", Ser. No. 719,232 filed 4-2-85 incorporated herein by reference. This system takes the digitally encoded signals and transmits them, along with power, through the skin into the implanted stimulator. The stimulator decodes the bit stream and delivers charge or current waveforms into electrodes implanted in the auditory nerve or cochlea.

It is an objective of the present invention to provide an improved power and data transmitter and related implanted receiver/stimulator.

The stimulating waveform must meet three safety requirements: charge balance, current limiting, and charge limiting. FIG. 1 illustrates two of these requirements as achieved in the prior art, FIG. 1A, and as achieved in the present invention, FIG. 1B. The waveforms are charge balanced; i.e., they are biphasic current pulses with equal areas enclosed under both phases. This is necessary because a net DC charge would promote bone growth that could destroy the neural tissue with which the stimulator is interfacing, rendering the implant useless. Also, a charge imbalanced waveform causes electrolysis at the surface of the implanted electrodes. Electrolysis ejects material from the electrode, and can lower the electrode lifetime from years to weeks. The stimulator must therefore recover all the charge delivered to an electrode to prevent neural damage and to insure an adequate implant lifetime.

The stimulators known in the prior art delivered many different types of waveforms, an example of which is shown in FIG. 1A. These stimulators metered the charge delivered by controlling the voltage on a capacitor that discharged into an electrode, an approach that controls charge but not current.

It is an objective of the present invention to provide a transmitter that controls both charge and current flow to the auditory nerves. There is evidence that high current densities can cause neural damage; the peak current of the capacitive discharge scheme combined with the electrode surface area has a current density in this damaging range.

Further, platinum electrodes which are those most commonly used and best adapted for implanting can only support a limited charge density before losing material, at or below 400 $nC/cm^2$. Therefore, it is an objective of the present invention to limit the charge density below this figure.

In summary, the safety requirements of the stimulating waveform must enforce charge balancing, charge limiting and current limiting to prevent possible neural damage.

Referring next to FIG. 2, FIGS. 2A and 2B show the waveform formats which were available with prior art stimulators. It is an objective of the present invention to provide the waveforms shown in FIGS. 2C, 2D and 2E, i.e., a quantized analog, a bipolar pulsatile (two rectangular waveforms that are 180° out of phase), and a monopolar pulsatile (rectangular) waveform.

Known prior art implantable stimulators fell into separate categories; it is an objective of the present invention to provide all three forms of stimulation.

Further, an adequate stimulator should have multiple separate stimulating outputs, possibly eight or more.

Another objective of the present invention to provide independent multi-channel operation, an ability lacking in many known stimulators. This is necessary because a successful stimulation algorithm will most likely require multiple independent channels to independently charge different auditory nerves.

Another objective of the present invention is to provide a system wherein the resolving power exceeds that of the auditory system. Early loudness difference tests showed that a subject could conclusively resolve down to 1.5 nC or charge difference between two stimulations. This charge increment combined with the 250 microamp maximum current means that the minimum timing increment for pulsatile stimulation should be about two microseconds. It is an objective of the present invention to provide an incremental timing resolution down to or below 2 microseconds.

Yet another objective of the present invention is to provide a system that is small, portable, and sufficiently efficient to operate for a full day on a set of transistor radio batteries so that it is convenient to use in a practical sense.

These and other objectives of the present invention are provided by the combination of a transmitter and implantable receiver wherein data is conveyed from transmitter to receiver utilizing a data format in which each channel to be stimulated is adapted to convey information in monopolar, bipolar or analog form.

The data format includes two types of code words: transition words in which one bit is assigned to each channel and can be used to create monopolar pulsatile or bipolar pulsatile waveforms; and amplitude words which can create analog waveforms one channel at a time.

An essential element of the output system is a current source digital to analog converter which responds to the code words to form the appropriate output on each channel. Each output is composed of a set of eight current sources, four with one polarity of current and the other four with the opposite polarity of current. In each group of four, the current sources are binarily related, I, 2I, 4I and 8I. In this arrangement each channel can supply 16 amplitudes times two polarities of current; meaning 32 current levels. This channel is simply a 5-bit digit to analog converter.

The output circuitry contains charge balance switches, something not normally seen in D-to-A converters. These switches are designed to recover residual charge when the current sources are off. They are also designed to current limit during charge recovery if the excess charge is too great so that they do not cause neural damage.

Each channel charge balances (will not pass DC current or charge) and charge limits to prevent electrode damage and bone growth. The charge balancing is performed by the charge balancing switches and by the blocking capacitor. The charge limiting is performed by the blocking capacitor only.

The charge level on each channel is defined using a switch network ladder which combines a plurality of parallel connected switches; closure of each switch doubles the current level handed off from the previous switch.

A number of other advantages of the present invention and features thereof will become apparent from the following detailed description which is given with reference to the following figures:

FIG. 1 illustrates the required properties of the stimulating waveform;

FIG. 2 illustrates examples of desired stimulating waveform;

FIG. 3 illustrates the data word format used to convey data from transmitter to receiver;

FIG. 4 is an illustration which shows schematically the implanted electronics of the auditory prosthesis;

FIGS. 5 and 6 are examples of waveforms which can be created using the subject system;

FIG. 7 shows the voltage regulators and FM demodulator which are coupled to the receiver portion of the stagger tuned coupling system;

FIGS. 8A and 8B show details of the logic chip and the timing to control the logic chip which detects and partially decodes the transmitted data;

FIGS. 9A and 9B show in simplified form and in detail the current source chip which responds to the outputs of the logic chip to provide the current signals over the electrodes to stimulate the auditory nerves.

The coding scheme used to control the implanted system will first be described with reference to FIG. 3. The three primary goals in designing this code are:

One, to account for failure mechanisms and limit their potential effects. This goal protects the subject from incorrect stimulation. It also prevents premature failure of the electrodes, and undue damage to the neural tissue.

Two, to minimize the number of bits needed to create a waveform, while maintaining the ability of producing a near arbitrary wave-shape. This goal reduces the chances of timing conflicts between closely spaced actions, lowers the minimum duration of an action, and expands the flexibility of the stimulator.

Three, to render the data less sensitive to component tolerance and drift. This goal increases the reproducibility and longevity of the implant.

The External Timing Control (ETC) Code is composed of the two words shown in FIG. 3, the "Transition Word" and the "Amplitude Word." Each word is eleven bits long and begins with a start bit. The data is sent on a serial bit stream with floating word frames, so the start bit indicates the beginning of a word. The parity bit checks for an odd number of bit errors in a word. The ID bit distinguishes between an "Amplitude Word" and a "Transition Word." The remaining eight bits contain state commands for the "Transition Word" and current level and address commands for the "Amplitude Word."

The "Transition Word" is intended to increase the flexibility of the system when used as a pulsatile stimulator, by addressing all eight channels of the multi-electrode stimulus array (FIG. 4) simultaneously. A pulsatile output has three possible states, both directions of current plus charge balancing. (Charge balancing means shorting the electrode to body ground, thereby recovering the residual charge left on it.) If, in a "Transition Word," a "one" appears in a given output's bit position, then that output cycles to its next state. If instead a "zero" appears, then that output holds its present state. All eight channels are represented by the last eight bits in the transition word, meaning that the system can simultaneously access them. If two outputs are programmed with opposite polarities of current, then switching them in unison creates a bipolar stimulation. With the "Transition Word" the stimulator can produce synchronized or staggered pulses, and it can act as a one to eight channel monopolar stimulator, or a one to four channel bipolar stimulator, or any mixture of the two types.

The "Amplitude Word" selects the pulsatile state sequence of a given channel. It is also used to create the arbitrary wave-shapes of an analog stimulator. This word is a standard Analog to Digital bit sequence. It has three bits to individually address the eight channels, four bits to adjust the current magnitude, plus one more bit to set the current polarity. The magnitude bits set the peak current of the pulsatile waveforms, while the polarity bit selects one of the two possible pulsatile sequences available for each channel: "sourcing current sinking current charge balancing," or "sinking current sourcing current charge balancing." The polarity bit coupled with the "Transition Word" determines whether a pair of channels deliver monopolar or bipolar stimuli (two synchronized channels with different state sequences can act as a bipolar pair). So the "Amplitude Word" selects the class of stimuli that a channel delivers.

The "Amplitude Word" is also capable of creating an arbitrary current wave-shape. Once the channels are activated by the "Transition Word" (switched from charge balancing to a current supplying state), the "Amplitude Word" can program 16 magnitudes and two polarities for each channel, creating a quantized analog approximation of the desired signal. At a one megabit per second data rate, the Nyquist sampling frequency for each of eight independent channels is 11,364 KHz, which means the maximum frequency that a channel could pass without aliasing a 5682 Hz, well above the 3 KHz cutoff frequency of a telephone channel (telephone quality bandwidth is generally considered necessary for adequate speech comprehension, without assuming a model for the speech production or decoding mechanism). So, under the worst case conditions, where all eight channels are operating as analog outputs, this code can still provide eight independent channels of quantized analog, each with telephone quality bandwidth.

Summarizing, the "Transition Word" is optimized for creating pulsatile stimulation. It can simultaneously address all eight channels and, with the help of the polarity bit in the "Amplitude Word," it can provide monopolar or bipolar stimulation. The "Amplitude Word" sets the current levels and state sequence of each channel. It can also create a quantized analog waveform on each channel. So this code provides all three classes of stimulation, monopolar pulsatile, bipolar pulsatile, and quantized analog.

This is an open loop system; information is sent in, but nothing is sent back out. The effects of errors are limited in two ways. First, the system is periodically resynchronized. Since the system is open loop, the external electronics must force the implanted electronics into a known state, after some time interval, to ensure that the two sub-systems agree. Synchronization is accomplished by transmitting an unused bit sequence of the "Transition Word." It is a "Transition Word" with no transitions. This special case is interpreted as a "Master Reset" that programs all the current sources to zero current, forces all the outputs into their charge balanced state, and clears all error conditions.

The periodic resetting is a "catch-all" approach for protection against unstoppable errors. One example of an unstoppable error is a coding mistake in the instructions sent to the package. These generally come from software bugs encountered while implementing a new algorithm or a new hardware system. This could deliver too much charge to an electrode, leave a current source "on," or deliver a charge imbalanced waveform. The implant volunteer requires protection from these potentially catastrophic mistakes. The ETC Code limits the effects of these mistakes by requiring at least one "Master Reset" every 5 ms to keep the package operational. Otherwise, the unit enters an error state, which is described later. This restriction bounds the effects of an error (detected or otherwise) to one 5 ms interval. It also initiates at least one attempt every 5 ms to charge balance all the electrodes correcting for any missed errors.

Second, upon detecting an error, the system programs all the current sources to zero, forces all the outputs into their charge balanced states, and enters an error state. The effect is similar to a "Master Reset" except that the package ignores all incoming commands. Only a "Master Reset" can clear the error state. By shutting down until the next resynchronization instead of continuing operation, the system has stopped an error from propagating into many errors. For instance, one biphasic pulse requires three "Transition Words." If one of those words contained an error that switched "on" the wrong channel, or did not switch the correct one, then an output would not return to its charge balanced state. Instead, it would continue supplying current, causing a charge imbalance on an electrode, and creating a potential source of failure. Here, one bit error has lost the synchronization between the outside and inside worlds, and later "Transition Words" are performing unintended tasks. So shutting down after detecting an error limits the effect of an error and prevents one error from growing into many.

There are three conditions that force the package into an error state: too long an interval between "Master Resets," parity errors, and a lost data stream. The reasons for detecting the "Master Reset" interval are already covered. The parity errors occur when the coils of the inductive link are too widely separated. Depending on the receiver design, the zero bits become ones, or the one bits become zeros. In either case, the data words are interpreted as all one type of bit. The words contain an odd number of bits, so the ETC Code forces even parity (at least one opposite bit in each word) to detect this condition.

FIG. 5 illustrates how to use the ETC Code to create a pulsatile waveform and the results of a detected error. The top line is the control word bit stream sent into the package. The next two lines are the current outputs of two channels of the stimulator. A pulsatile waveform generally relies heavily on "Transition Words" as shown in this example. The "Master Reset" is first sent into the package to clear any error conditions and to synchronize the system. Next, two "Amplitude Words" set the polarity and magnitude that the current sources of channel 1 and channel 5 deliver when they are turned "on." Next, a "Transition Word" switches these two channels out of their charge balanced state, simultaneously. The switching occurs one bit period after the word is received. Then two more "Transition Words" complete the state sequence for channel 5. Finally, another "Transition Word" attempts to cycle channel 1 to its next state. But the word contains a parity error that force all the outputs into their charge balancing state to recover any residual charge, and the package halts in an error state, where it stays until another "Master Reset" is sent. So once the magnitude and polarity of a pulsatile waveform are programmed, "Transition Words" control the timing of the current source switching. Since they can switch up to eight channels at a time, few timing conflicts should arise.

FIG. 6 is an example of the ETC Code producing a quantized analog wave-shape. While the pulsatile example relied primarily on "Transition Words," creating arbitrary waveforms usually requires using the "Amplitude Word." The top line of the figure is the input data word stream and the lower line represents the current output of one channel. Again, a "Master Reset" is sent to clear and synchronize the package. Then a "Transition Word" is sent to turn the current source "on." No current is delivered because the "Master Reset" programmed the outputs to zero current. Now "Amplitude Words" are sent to construct a waveform in a typical D to A pattern. Finally, another "Master Reset" is sent to keep the system from timing out (remember, no more than 5 ms are allowed between "Master Reset" words) and to recover residual charge on the electrodes. So the ETC Code can create analog as well as pulsatile waveforms.

The ETC Code was designed to reduce the number of bits needed to create a signal (or event). By pruning the unnecessary information from the data, the word length is reduced, allowing the transmission of more instructions per unit of time.

To achieve this goal, the ETC Code transmits the state information in the control words and the timing information in the temporal position of each word. In other words, when an action is required, a word specifying the state of one or more currents is sent, and the action occurs one bit cycle after the word is received. Thus, bits containing temporal information (pulse width, pulse position, pulse period, etc.) are unnecessary.

The ETC Code also takes advantage of advance knowledge about the pulsatile wave-shapes (monopolar and bipolar) to further reduce the number of bits needed to create these waveforms. Each output channel has three possible pulsatile states, "sourcing current," "sinking current," and "balancing charge." Defining three states per channel for an eight channel system normally requires 16 bits. But the need for charge balancing generally locks the outputs into the sequence of "current; opposite polarity current; charge balancing." By specifying a state *transition* instead of an *absolute* state, only one bit per channel is needed; cutting the number of data bits from 16 to 8. In other words, the control word does not tell a channel explicitly what job to do. Instead, it tells the channel to stop whatever it is doing and move on to its next job, without stating what the next job is.

Summarizing, bits containing the timing and the absolute state information are unnecessary for this code, allowing a significant increase in the number of instructions per unit of time.

The bit stream is encoded using pulse-duration-modulation. In this case, a long pulse is a "one" and short pulse is a "zero." PDM was chosen because the leading edge contains the timing (synchronizing) information, and the simple circuit that decodes it can also use this information to generate the internal clock. By combining the detector and clock into one circuit, the system gains temporal flexibility, reduces its sensitivity to component variations, and saves power.

Since the clock period is set by the period of the incoming bits, the user can change the temporal resolution of the package without altering the implanted electronics. In fact, the package can track any data rate slower than its maximum; even to DC (although it flags a bit stream "time out" error when the bit period exceeds 22 $\mu$s). This approach has added the capability of modulating the temporal position of a waveform, and eliminates the requirement of locking a waveform's transitions to a fixed clock period, such as 1 $\mu$s/bit.

Another advantage of this approach is that it eliminates the problem of synchronizing two clocks, one internal and one external. Though normally not a major problem, it can become serious as components age and time constants change. The package is intended to operate for 10 years, long enough for these problems to surface. By maxing the timing accuracy dependent only on the external electronics, the system should have a dependable clock period for the full 10 years.

Finally, if high clock speeds are unnecessary, then slowing the clock rate of the system lowers its power consumption. This ability may open a wider range of applications for this stimulator, such as muscle control, or pain suppression.

The choice of pulse-duration-modulation simplifies the detector/clock circuitry, adds the capability of temporal modulation, desensitizes the system to component aging and drift, and allows a reduction in the power consumption of the system that may open new applications.

The coupling from the transmitter for this data (which may be of any well-known design) to the implanted receiver is disclosed in the incorporated patent application of Galbraith, et al.

The stagger-tuned link produced a fairly stable output voltage from which to create a regulated voltage supply. Ideally, an efficient voltage regulator would operate with a small voltage dropped across it, so that it consumes little power while sourcing large currents. It should also burn a negligible amount of quiescent current for its own operation. The regulators used in the stimulator are close to this ideal. Their circuit diagrams are shown in FIG. 7. These voltage regulators function down to one saturated bipolar transistor drop (0.3 volts) across them at full load current; the quiescent current consumption for both regulators is about 0.25 mA, less than 10 percent of the total stimulator current (3.3 mA maximum).

These regulators are capable of both sourcing and sinking current. This capability provides general protection for the implanted electronics if excessive voltages occur from design oversights. It was added to reduce or eliminate the potential effects of any design oversights.

This section describes the circuitry that converts the information sent by the ETC Code into stimulation patterns on the electrodes is disclosed with reference to FIGS. 8, 9 and 10. It covers, in detail, the implementation of the safety requirements. It also provides examples showing the achievement of the principal design goals; producing all three classes of stimulation for flexibility, arbitrary wave-shape for experimental needs, and independent multi-channel operation.

The logic chip of FIG. 8 performs the decoding of the PDM data stream and most of the ECT Code. The circuit diagram is shown in FIG. 8A and an example timing diagram is shown in FIG. 8B. The PDM decoding is done simply by a D-flip-flop and a one-shot. The rising edge of the PDM signal fires the one-shot and the data is detected on the falling edge by the flip-flop. The one-shot also acts as the clock so that the internal clock tracks the data rate, allowing temporal modulation of the switching information. This simple circuit not only performs detection and clock generation; it also eliminates the need for an accurate internal timing reference since it derives this information from the outside world.

The rest of the chip contains the state machines for all eight channels, the logic to decode most of the ETC coded bit stream, and implements most of the protection conditions of the ETC Code. This chip explicitly decodes the transition word that drives the output state machines and that carries the Master Reset. This chip performs the "power on reset," parity checking, and lost bit stream detection. The interface between it and the current source chip performs the Master Reset time-out detection.

This design is fairly conservative to improve the chances of successful operation. As examples, the circuitry is fully clocked to avoid race conditions. It uses cellular elements to minimize the layout mistakes. The clocking one-shot is insensitive to the duration of a bit so that different data rates will not affect the detection period. The transistors are operated nearly two orders of magnitude below their maximum switching frequency so that the circuit can tolerate a large variation in the fabrication process.

To reduce the power consumption of the system, the logic chip operates at a lower power supply voltage than the current source chip. The logic chip only needs 5 volts of the 13-volt supply to function. Since the power drawn by a CMOS circuit tends to increase with the square of the voltage, the lower supply cuts the power consumption significantly.

To further reduce the power used, the control lines connecting the logic chip to the current source chip are only active when sending information. The current source chip must level shift all the incoming signals from the logic chip and level shifters consume power. So the conservative design ensures safe operation and saves power.

The logic is implemented using a CMOS gate array (SPI 7005B) from Semi Processes Incorporated. The array contains roughly 5000 transistors of which about 3000 are used to implement the system logic using known gate array connection techniques.

The current source chip of FIG. 9 performs the final decoding of the amplitude word and provides the coding to current interface to the electrodes. It, along with a few external components, also ensures the safety of the implant by limiting the current and charge, and by providing charge balancing.

FIG. 9A shows a conceptual diagram for one channel. There are eight current sources per channel. They are divided into two groups of binarily related values (I, 2I, 4I and 8I), giving 16 magnitudes and two polarities. The switches $S_o$ through $S_3$ set the magnitude of the current under control of the Amplitude Word. The switches $S_{in}$ and $S_{out}$ determine the polarity and are primarily controlled by the transition word. Each channel is capable of providing a pulsatile or quantized analog output depending on the switching sequence of these pass gates. For example, to produce a monophasic pulse, simply program the current sources (say turn on $S_1$ and $S_2$), then alternately switch $S_{out}$ on and $S_{in}$ on.

The blocking capacitor $C_B$ is an external component that is probably the most important safety element of each stimulating channel. It stops DC current from passing into the electrode. DC current would eventually destroy the electrode, possibly damage the nerves, and promote bone growth. The capacitor $C_B$ also acts as a charge limiter. Excessive charge (about 400 nC/phase in this case) causes the electrodes to break down. This capacitor limits the worst case charge to about 300 nC/phase. Finally, since this capacitor is a high reliability pace maker part and since it is the last component between the stimulator and the electrodes, it limits the effects of failures in the electronics leading to the electrodes (such as limiting the output charge of a current source that is stuck "on"). So this capacitor limits the charge, blocks the DC current, and protects against component failures; all of which should prevent damage to the electrodes and nerves.

Notice that $S_{in}$ and $S_{out}$ have two complementary switches that can short the output to ground. These switches and the blocking capacitor ensure the charge balancing. Once the current sources have completed delivering current, any residual charge left on an electrode appears as a voltage across the blocking capacitor. By shorting the output, that charge is recovered.

The current and charge limits of this system are not locked by the integrated circuits. Instead, they are programmed by components external to the chip (but still inside the implanted package). This arrangement allows for adjusting the stimulator to new electrodes or new uses. For example, a larger electrode surface area could support higher currents and more charge than the present system is set for. The maximum output charge is determined by the power supply voltage and the size of the blocking capacitor, so a new blocking capacitor sets a new maximum output charge. To understand how the maximum current is adjusted, look at the circuit diagram for the current source chip shown in FIG. 9B. Notice that the reference current for all the current sources is set by one external resistor RI. A new resistor sets a new current peak. Therefore, even though the chips are static, the stimulating characteristics of the system are programmable (at least until the package is sealed) and can match the needs of future implants.

In summary, the system is conservatively designed in an effort to promote reliability. It provides safety and a long electrode lifetime by limiting the current and charge, by blocking any DC current, and by charge balancing. Its current and charge limits are reprogrammable allowing it to adapt to future needs. It is flexible, capable of producing monopolar, bipolar, and analog outputs with few limitations in each class. It can create nonstandard waveforms for research needs, and it provides eight independent channels of stimuli. In summary, it has met its primary goals of safety and flexibility.

What is claimed is:

1. A neural stimulator comprising a transmitter, an implantable receiver and means for coupling the output of said transmitter to said receiver, said receiver including a plurality of output channels to the nerves of the wearer, said receiver including means for simultaneously addressing each of said channels in monopolar or bipolar mode, or alternatively in analog mode to stimulate said nerves.

2. A stimulator as claimed in 1 wherein said receiver includes a current source device coupled to each of said channels, said current source device comprising a switch network, the number of closed switches selectively defining the charge and current envelope on any channel.

3. A stimulator as claimed in claim 2 further comprising a charge balancing switch cooperating with each of said current source devices and blocking capacitors for eliminating charge imbalance into the electrode channels.

4. A stimulator as claimed in 1 wherein said addressing means further comprise means for defining a quantized analog current waveform on any of said channels.

5. A stimulator as claimed in claim 1 further comprising a multi-electrode stimulus array connected to the output channels of the stimulator.

6. A stimulator as claimed in claim 5 including means for establishing transition words for defining a binary state on each of said channels, and means for creating amplitude words for defining an analog signal on any of said channels.

7. A stimulator as claimed in claim 5 wherein said means for establishing a transition word simultaneously address all of said plurality of channels.

8. A stimulator as claimed in claim 7 wherein said means for establishing a transition word comprise means for transmitting an unused bit sequence for synchronizing all of said channels.

9. A stimulator as claimed in claim 7 wherein said means for establishing a transition word cooperate with a polarity bit from the means for establishing an amplitude word to provide monopolar or bipolar stimulation on each of said channels.

* * * * *

UNITED STATES PATENT AND TRADEMARK OFFICE
CERTIFICATE OF CORRECTION

PATENT NO. : 4,592,359

DATED : June 3, 1986

INVENTOR(S) : Douglas C. Galbraith

It is certified that error appears in the above-identified patent and that said Letters Patent is hereby corrected as shown below:

Column 1, line 1, insert the following paragraph:

--The U.S. Government has a paid-up license in this invention and the right in limited circumstances to require the patent owner to license others on reasonable terms as provided for by the terms of Contract Numbers N01-NS-1-2354 and N01-NS-5-2306 awarded by the National Institutes of Health.--

Signed and Sealed this

Twentieth Day of October, 1992

Attest:

DOUGLAS B. COMER

*Attesting Officer*   *Acting Commissioner of Patents and Trademarks*